United States Patent [19]

Fujii

[11] Patent Number: 5,419,825
[45] Date of Patent: May 30, 1995

[54] BASE SEQUENCING APPARATUS

[75] Inventor: Hidehiko Fujii, Kyoto, Japan

[73] Assignee: Shimadzu Corporation, Kyoto, Japan

[21] Appl. No.: 961,533

[22] Filed: Oct. 15, 1992

Related U.S. Application Data

[63] Continuation-in-part of Ser. No. 737,416, Jul. 29, 1991.

[30] Foreign Application Priority Data

Oct. 18, 1991 [JP] Japan ................................. 3-299917

[51] Int. Cl.⁶ ............................ C25B 7/00; C25B 9/00
[52] U.S. Cl. .............................. 204/299 R; 204/182.8; 364/413.01; 435/6
[58] Field of Search ........................ 204/299 R, 182.8; 364/413.01; 435/6

[56] References Cited

U.S. PATENT DOCUMENTS 4,720,786 1/1989 Hara ............................... 364/413.01

FOREIGN PATENT DOCUMENTS 198403 10/1986 European Pat. Off. .
1080852 3/1989 Japan .

OTHER PUBLICATIONS

Lance B. Koutny and Edward S. Yeung, "Automated Image Analysis for Distortion Compensation in Sequencing Gel Electrophoresis" Applied Spectroscopy, vol. 46, No. 1 (Jan. 1992) 136-141.

Philip Taylor et al "Computer assisted size measurement on digitising tablet of nucleic acid and protein molecules from gels" Journal of Biochemical and Biophysical Methods, 14 (1987) 71-83.

Primary Examiner—John Niebling
Assistant Examiner—C. Delacroix-Muirheid
Attorney, Agent, or Firm—William L. Klima

[57] ABSTRACT

An on-line system base sequencing apparatus wherein calibration coefficients for time bases of respective electrophoresis lanes are evaluated from differences between positions of signals already outputted in a range causing no sequence inversion and positions of substantially regular intervals for originally outputting signals, and time bases as to the respective electrophoresis lanes are calibrated with the calibration coefficients, thereby obtaining correct base sequence. Thus, the bases can be correctly sequenced even if electrophoresis speed differences are caused between the electrophoresis lanes.

18 Claims, 11 Drawing Sheets

FIG.5

A(1000), G(1000), T(1000), C(1000), SEQ$(1000)

| NUMBER | 11 | 12 | 13 | 14 | 15 | 16 | 17 | 18 | 19 | 20 | 21 |
|---|---|---|---|---|---|---|---|---|---|---|---|
| A(1000) | 2020 | 0 | 0 | 0 | 0 | 0 | 0 | 0 | 0 | 2200 | -- |
| G(1000) | 0 | 2050 | 0 | 0 | 0 | 2130 | 0 | (2170) | 0 | 0 | -- |
| T(1000) | 0 | 0 | 2055 | 2075 | 0 | 0 | (2135) | 0 | 0 | 0 | -- |
| C(1000) | 0 | 0 | 0 | 0 | 2100 | 0 | 0 | 0 | (2180) | 0 | -- |
| SEQ$(1000) | A | G | T | T | C | G | T | G | C | A | -- |

BASE SEQUENCING APPARATUS

This is a continuation-in-part of application Ser. No. 07/737,416 filed Jul. 29, 1991.

BACKGROUND OF THE INVENTION

1. Field of the Invention

The present invention relates to an on-line system base sequencing apparatus for introducing nucleic acid fragment samples, which are pretreated by the Sanger method using fluorescent primers (primers obtained by chemically bonding fluorescent materials as markers), into a sample introducing part of a slab type gel of a gel electrophoresis apparatus in units of end bases. The samples are simultaneously electrophoresed and the fluorescence is detected during the electrophoresis by excitation using an optical detection system that scans in a direction perpendicular to the electrophoresis direction. The base sequencing is then performed with a data processing unit programmed to carry out a number of functions to prevent the effects of smiling.

2. Description of the Background Art

In an on-line system base sequencing apparatus using a slab type gel, nucleic acid fragments which are previously treated by the Sanger method are electrophoresed in different electrophoresis lanes in response to the types A (adenine), G (guanine), T (thymine) and C (cytosine) of the end bases thereof.

In general, a gel electrophoresis apparatus creates an undesirable so-called "smiling" effect, which is a phenomenon wherein the electrophoresis speeds vary with electrophoresis lanes. If the signals are successively read from the electrophoresis lanes for the end bases A, G, T and C and the samples are directly base-sequenced with out accounting for the "smiling" effect, the sequence can be inverted and result in misreading thereof.

It is believed that "smiling" is mainly caused by varying temperature distributions in the electrophoresis lanes caused by Joule heating, which is generated as the result of electrophoresis. In order to prevent "smiling", there has been proposed a method wherein a metal plate is placed in close contact with the electrophoresis plate thereby evening the temperature distribution. Another methods of solving varying temperature distributions in the electrophoresis lanes involves storing the electrophoresis plate in a closed container and supplying air controlled at a constant temperature thereby homogenizing the temperature, as disclosed in Japanese Patent Laying-Open Gazette No. 2-143145 (1990).

While the mobility difference between 500 bases and 501 bases is 0.2% (=1/500), for example, it is necessary to control any temperature irregularity to be not more than 0.1° C. in order to suppress the mobility difference caused by "smiling" to be not more than 0.2% by temperature control. In practice, this type of temperature control is very difficult to maintain.

Another problem associated with conducting a base electrophoresis involves electrophoresis gel containing electrolytic ammonium persulfate as a catalyst, which tends to migrate toward the side of an external electrode buffer following electrophoresis. If the concentration of this electrolyte is varied with position, differences in ionic strength can occur between the different electrophoresis lanes resulting in "smiling." This type of "smiling" resulting from non-heterogeneous concentration of the electrolyte cannot be prevent by temperature control.

In addition to the aforementioned types of "smiling", misreading of the base sequence is also caused by non-heterogeneous sample introduction slots of the electrophoresis lanes. In general, electrophoresis distances (i.e. distances between sample introduction slots and a detection part) of an on-line system fluorescent DNA sequencing apparatus are about 200 to 500 mm. At the sample introduction slots, sample positions can easily be displaced by 1 to 2 mm from each other by differences in horizontal position of the gel formation, penetration of urea within the slots, and the like. A difference of 1 mm at the sample introduction slots corresponds to a difference of 0.2% (1/500) assuming the electrophoresis distance to be 500 mm. This is equal to the mobility difference between bases 500 and 501. It is impossible to prevent such mobility difference by temperature control.

SUMMARY OF THE INVENTION

An object of the present invention is to provide an improved base sequencing apparatus.

Another object of the present invention is to provide a base sequencing apparatus, which can correctly sequence bases even if mobility differences between lanes result from "smiling" or the like.

According to the present invention, calibration coefficients for time bases of respective electrophoresis lanes are evaluated from differences between the positions of signals already outputted in a range that no sequence inversion is caused, and positions of substantially regular intervals for original outputting signals, and calibrating subsequent time bases for the respective electrophoresis lanes with the resulting calibration coefficients, thereby attaining the correct base sequence.

As shown in FIG. 1, a data processing unit for the inventive base sequencing apparatus comprises: signal storage means 40 for storing signals from respective electrophoresis lanes with respect to time; maximum signal time detection means 42 for detecting time providing maximum values of signals as to the respective electrophoresis lanes; maximum signal time storage means 44 for storing the maximum signal times; appearance time estimation means 46 for calculating appearance times of the maximum signals from the electrophoresis lanes other than a reference lane selected from four (4) electrophoresis lanes appearing between two maximum signals of the reference lane on the assumption that there is no difference of mobility between the electrophoresis lanes; calibration coefficient calculation means 48 for calculating calibration coefficients from ratios of the maximum signal times of the three (3) electrophoresis lanes calculated in the appearance time estimation means 46 to actual maximum signal times; time base calibration means 50 for calibrating the time bases of the three electrophoresis lanes with the calibration coefficients; and base sequencing means 52 for performing base sequencing from the maximum signal times of the reference lane and the three (3) electrophoresis lanes based on the calibrated time bases.

The appearance time estimation means 46 performs calculations on the assumption that the maximum signals of the three (3) electrophoresis lanes appear between two maximum signals of the reference lane at regular intervals, for example.

In order to update the calibration coefficients, a calibration coefficient is calculated every time a maximum signal appears on the reference lane between this signal and a maximum signal appearing on the reference lane immediately ahead thereof. Then, the time bases of the remaining three (3) electrophoresis lanes, which are effective until a next maximum signal appears on the reference lane, can be calculated with the updated calibration coefficient.

In an on-line system base sequencing apparatus, signals appears in order of length (e.g. from short nucleic acid fragments to long nucleic acid fragments) with the lapse of time. While the signals themselves are broad and sequence misreading by sequence inversion is easily caused by "smiling" in subsequently appearing long nucleic acid fragments, the signals are sharp in previously appearing short nucleic acid fragments with no sequence inversion occurring even if there exists "smiling" resulting in no misreading. When short nucleic acid fragments have already appeared, however, displacement from positions of original appearance (i.e. positions at regular time intervals) occurs if "smiling" takes place, however, with no sequence inversion.

As shown in FIG. 8, a data processing unit for a base sequencing apparatus according to the present invention comprises signal storage means 40 for storing signals from respective electrophoresis lanes with respect to time; maximum signal time detection means 42 for detecting time values providing maximum values of signals as to the respective electrophoresis lanes; maximum signal time storage means 44 for storing the maximum signal times; appearance time estimation means 46 for calculating appearance times of maximum signals of the electrophoresis lanes other than a standard lane, being selected from four (4) electrophoresis lanes, appearing between two maximum signals of the standard lane with the time base of the standard lane on the assumption that there is no difference of mobility between the electrophoresis lanes; calibration coefficient calculation means 48 for calculating calibration coefficients from ratios of the maximum signal times of the three (3) electrophoresis lanes calculated in the appearance time estimation means 46 to actual maximum signal times, means 101 for converting time bases of signals in time domains other than those used for calculating the calibration coefficients through the calculated calibration coefficients; means 102 for deciding validity of the calibration coefficients depending on whether or not the as-converted signals appear at uniform time intervals; total time base calibration means 50 for calibrating the total time bases of the three (3) electrophoresis lanes through calibration coefficients being decided as being valid; and base sequencing means 52 for performing base sequencing from the maximum signal times of the four electrophoresis lanes based on the calibrated time bases. The appearance time estimation means 46 performs calculations on the assumption that the maximum signals of the three (3) electrophoresis lanes appear between two maximum signals of the standard lane at regular intervals, for example.

Means 103 is adapted to change calculation domains for re-calculating calibration coefficients, when the means 102 decides that the calibration coefficients are invalid.

Means 104 is adapted to change the standard lane when all calibration coefficients of the three (3) lanes are not decided to be valid with respect to the set standard lane.

In an on-line base sequencing apparatus, signals appear in order from the shortest nucleic acid fragment to the longest fragment, as shown in FIG. 9. Referring to FIG. 9, curves for lanes 1, 2, 3 and 4, which must originally be absolutely identical, are separated from each other due to temperature irregularity. If the temperature irregularity is in a stationary state, however, the curves are in such proportional relationship to each other that the ratio a1 to a2 is constant at every point. As understood from FIG. 9, signals themselves are broad and base sequences are easy to misread (inverted) due to "smiling" as to long nucleic acid fragments appearing later (see sampling points 4, 5 and 6 in FIG. 9), while signals are sharp and no inversion nor misreading of base sequences takes place even if "smiling" is caused, as to short nucleic acid fragments appearing in advance (refer to sampling points 1, 2 and 3 in FIG. 9). When the short nucleic acid fragments have already appeared, however, there is recognized displacement from the original appearance positions (positions substantially at regular time intervals) if "smiling" is caused, although the base sequences are not inverted.

According to the present invention, calibration coefficients for time bases of respective electrophoresis lanes are obtained from displacement between positions of already appearing signals in a range causing no inversion of base sequences and original signal appearance positions which are substantially at regular intervals so that time bases for the subsequent respective electrophoresis lanes are calibrated through the as-obtained calibration coefficients, thereby attaining correct base sequencing.

Although the signals are correctly obtained in such an apparatus, peaks may simultaneously appear on a plurality of lanes due to a chemical cause, or vertical positions of the peaks may be so non-uniform that the signals are incorrectly recognized to cause erroneous evaluations. The means 101, 102 and 103 shown in FIG. 8 are adapted to confirm validity of the temporarily calculated calibration coefficients by applying the same to other time domains. Thus, the calibration coefficients are improved in accuracy, thereby improving accuracy of the base sequencing.

According to the present invention, one of the electrophoresis lanes for A, G, T and C is selected as a reference lane so that the time bases of the remaining three (3) electrophoresis lanes are calibrated with reference to the distance between two peaks of the reference lane. Thus, it is possible to correctly sequence bases even if there are differences between electrophoresis speeds of the electrophoresis lanes due to "smiling" or the like.

Further, the inventive method can cope with intermediate changes of electrophoresis states. Also, the present invention can also cope with "smiling" resulting from a cause other than varying temperature distributions.

The present invention can further cope with a system of taking data and sequencing bases successively from data taken in a multitask manner.

The present invention can be combined with a method of homogenizing temperatures by ambient air control. The accuracy is further improved in this case. Further, the foregoing invention can be combined with a method of homogenizing temperatures by ambient air control. The accuracy is further improved in this case.

The data processing unit of the base sequencing apparatus according to the present invention can be programmed with conventional computer software to carry out the above described functions in various manners. One skilled in the art of programming equipment of this nature can design the requisite program without undo experimentation, or without special skill or knowledge based on the information contained in this disclosure.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 illustrates exemplary maximum value data and definitive base sequence;

DETAILED DESCRIPTION OF PREFERRED EMBODIMENTS

Figure 1:
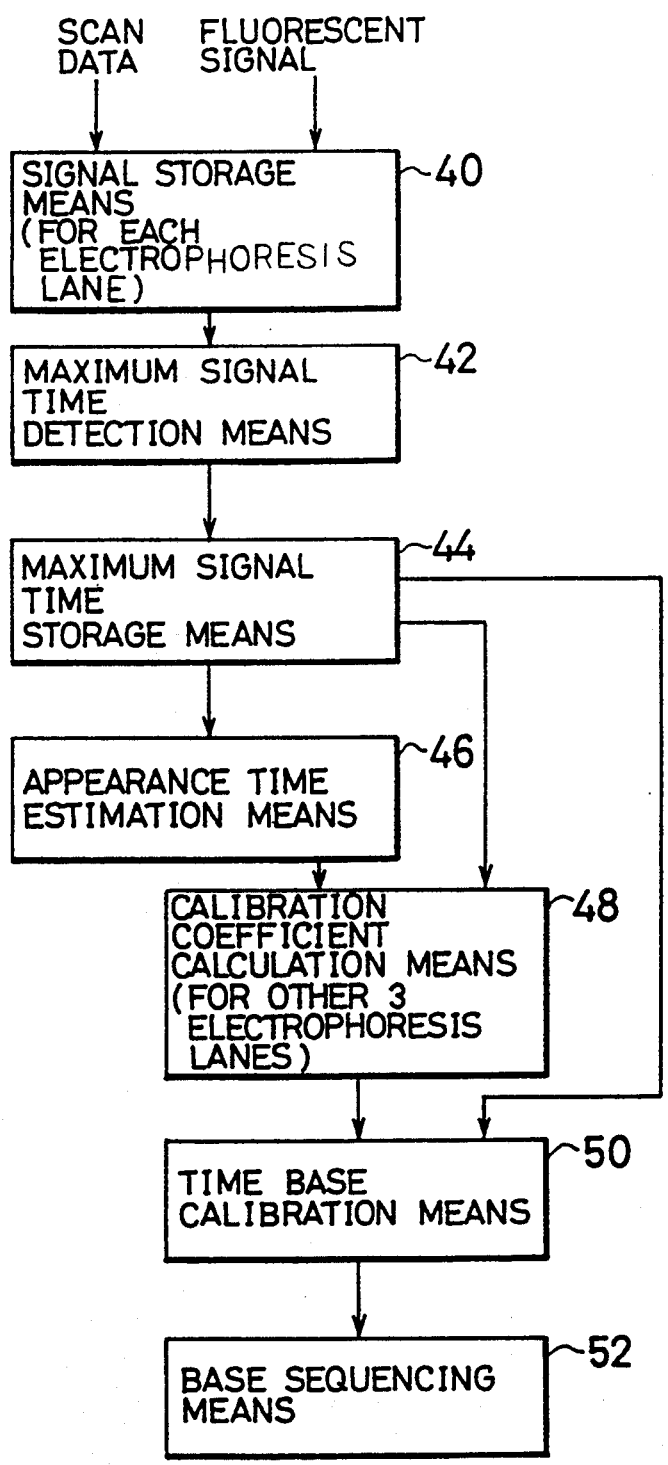
FIG. 1 is a block diagram showing functions of a signal processing microcomputer in an embodiment of the present invention.
Figure 2:
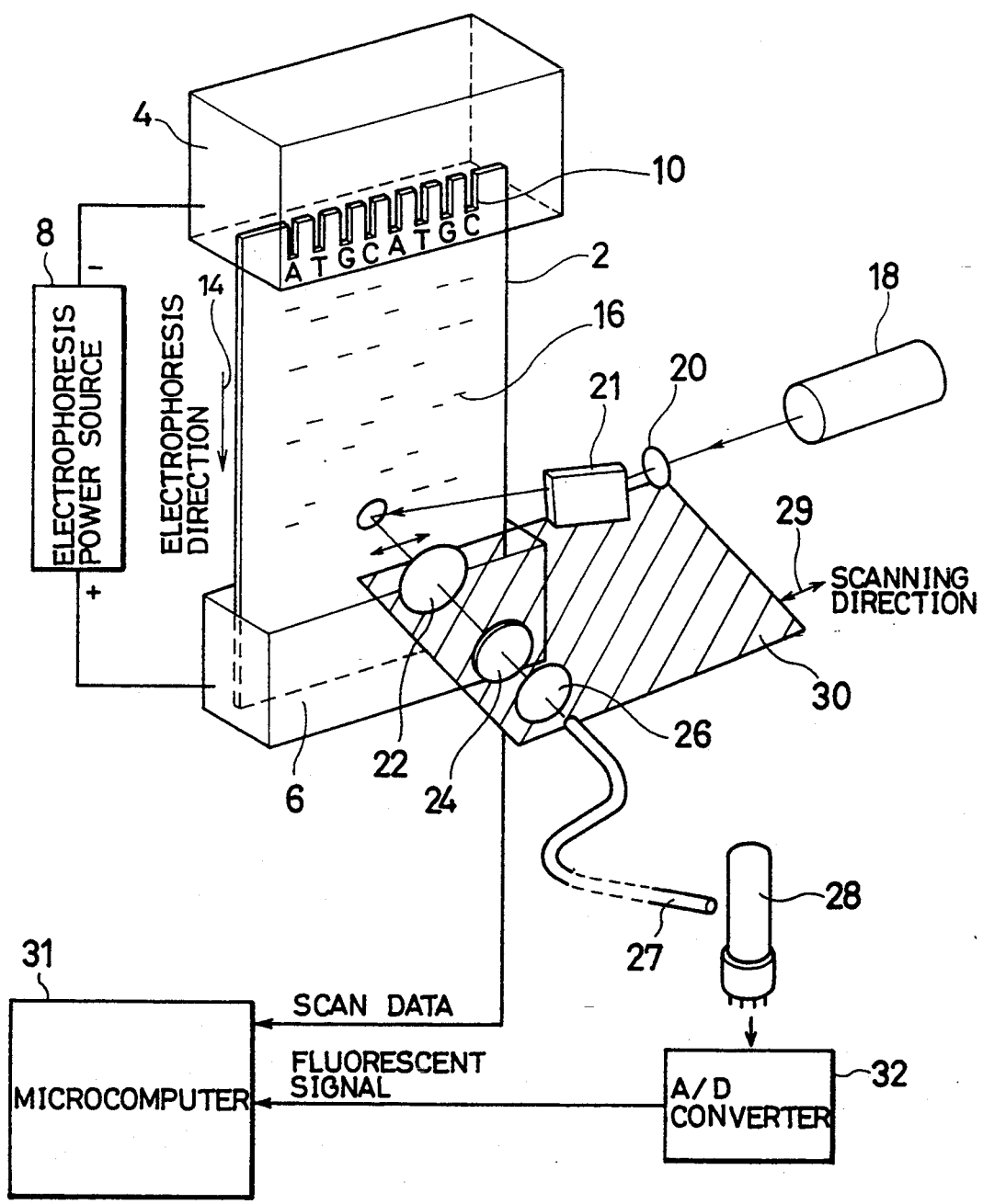
FIG. 2 is a perspective view schematically showing the embodiment.

An embodiment of the base sequencing apparatus according to the present invention is shown in FIG. 2.

A slab-type electrophoresis gel 2 is prepared from a polyacrylic amide gel. Both ends of the electrophoresis gel 2 are dipped in electrode layers 4 and 6, which contain electrolytic solutions. An electrophoresis power source 8 applies an electrophoresis voltage across the electrode layer 4 and 6.

Sample introduction slots 10 are provided in one end of the electrophoresis gel 2 in order to inject samples. Samples of respective end bases are introduced into prescribed positions of the respective slots 10. These samples are prepared from four types of DNA fragments which are labelled by FITC, being a fluorescent material, by a well known method and so treated that respective bases A, G, T and C come to ends by the Sanger method. The FITC is excited with an argon laser beam of 488 nm in wavelength, and generates fluorescence of 520 nm in wavelength.

When the power source 8 applies the electrophoresis voltage, the samples are electrophoresed in the electrophoresis gel 2 with time in an electrophoresis direction 14 as electrophoresis bands 16 separate and reach the measuring portion.

The measuring portion is provided with an excitation system for applying excitation light from an argon laser 18, which emits a laser beam of 488 nm in wavelength, by a condenser lens 20 and a mirror 21, and a detection system for collecting fluorescent light generated from fluorescent materials forming the electrophoresis bands 16 which are present in positions irradiated with the exciting laser beam by an objective lens 22 and detecting the fluorescent light by a photomultiplier 28 through an interference filter 24 of 520 nm, a condenser lens 26 and an optical fiber tube 27. The excitation and detection optical systems including the condenser lens 20, the mirror 21, the objective lens 22, the interference filter 24, the condenser lens 26 and the optical fiber tube 27 are provided on a scanning stage 30, which mechanically moves to scan on a measuring line in a direction (scanning direction 29) where the position irradiated with the excitation light beam intersects with the electrophoresis direction 14 every constant period.

Detection signals (fluorescent signals) from the photomultiplier 28 are incorporated in a signal processing microcomputer 31, which is a data processing unit, through an amplifier and an A-D converter 32. The microcomputer 31 also incorporates signals corresponding to positions irradiated with the excitation beam on the measuring position of the electrophoresis gel 2 as scan data. Thus, the overall fluorescent signals obtained by scanning of the excitation and detection optical systems in the scanning direction are incorporated in the microcomputer 31 with position information.

The operation of this embodiment is now described with reference to FIGS. 3, 4 and 5.

Figure 3:
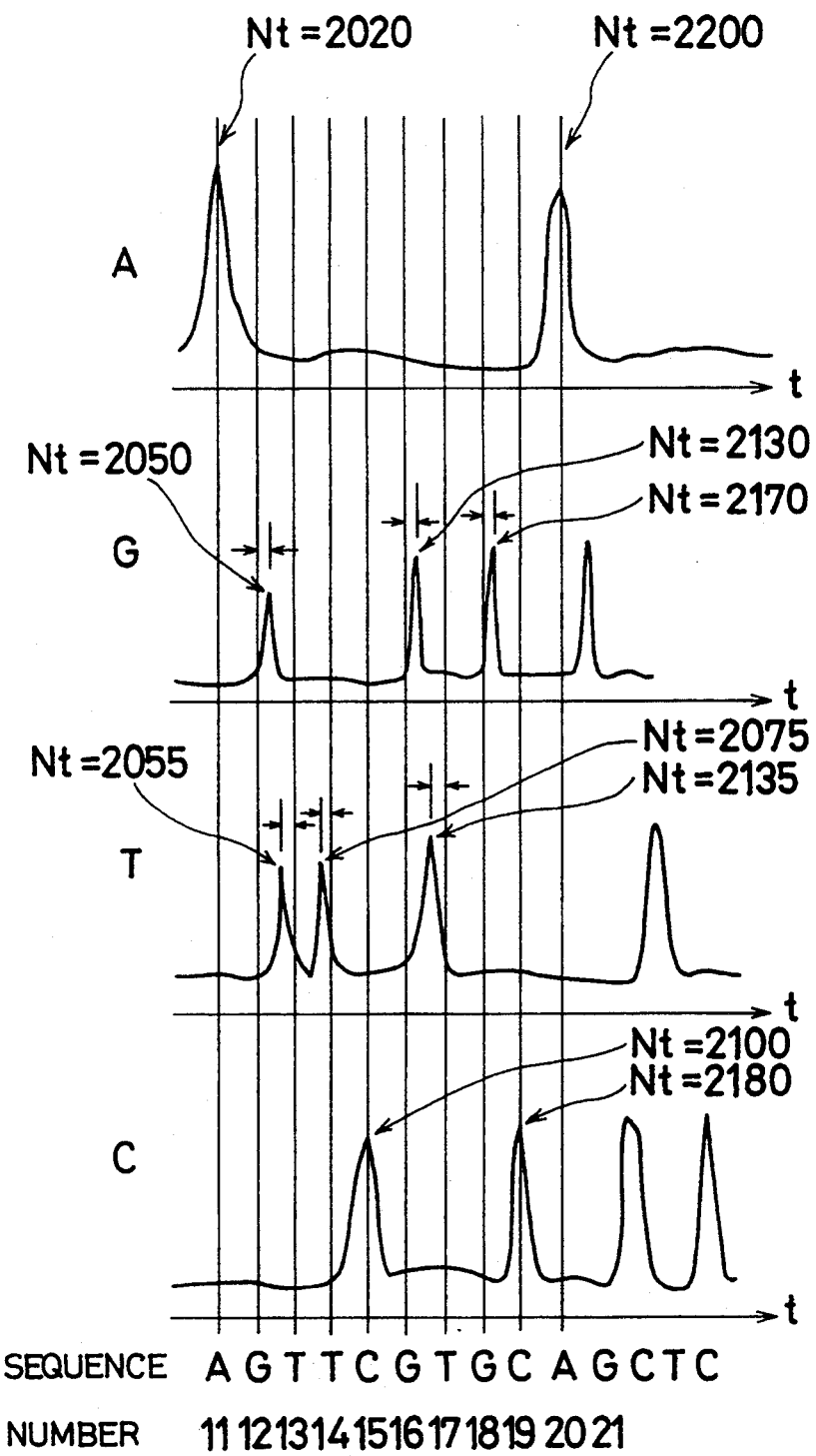
FIG. 3 illustrates signals of respective electrophoresis lanes measured in the embodiment.

FIG. 3 shows exemplary signals obtained in the base sequencing apparatus shown in FIG. 2. Symbols A, G, T and C correspond to the respective electrophoresis lanes, while the symbol Nt represents numbers of scannings made by the optical systems in the scanning direction.

FIG. 3 shows portions having relatively short base lengths, and no inversion of signal appearance order, i.e., sequence misreading is caused even if smiling takes place, since the difference between electrophoresis speeds per base length is relatively large. Referring to FIG. 3 in more detail, however, eight peaks of G, T and C are present between 11-th and 20-th peaks of A. When lines are drawn on the assumption that the eight peaks appear between the two peaks of A at regular intervals, it is understood that the peaks of G are delayed from the lines and the peaks of T appear slightly ahead of the lines although the peaks of C are present substantially on the lines.

When samples are electrophoresed under a constant voltage, the peaks will not appear strictly at regular intervals in the structure shown in FIG. 2. However, when time bases are calibrated between two peaks of a certain reference electrophoresis lane, i.e., the lane of A in this case as shown in FIG. 3, approximation of such regular intervals is sufficient since the interval between the two peaks of the reference lane is about 20 to 30 bases at the most.

As to the signals shown in FIG. 3, it is obvious that the appearance order is inverted in due course of time to cause errors in base sequencing since the peaks of G are delayed and those of T are ahead as compared with those of A and C.

Procedures for calibrating the time bases is now described with reference to a flow chart shown in FIG. 4.

In an initial state, the detected signals of A, G, T and C shown in FIG. 3 are in sequence RA(16000), RG(16000), RT(16000) and RC(16000). Dimensions RA(16000), RG(16000), RT(16000) and RC(16000) define an array of digitalized values of detected phosphorescence signals as to the electrophoresis lanes of A, G, T and C, respectively. The sequence RA(16000) starts from RA(0). This also applies to other sequence RG, RT and RG. However, the sequence RG, RT and RG are rewritten in accordance with progress of the program.

Initial values of sequence A(1000), G(1000), T(1000) and C(1000) for storing maximum value date are zero, and peaks are so numbered that an M-th peak appearing on G is G(m). Initial values of calibration coefficients Kf, Kt and Kc are set at 1. Signals for which time bases are calibrated as to the electrophoresis lanes of G, T and C are temporarily stored in sequence RG1(16000), RT1(16000) and RC1(16000), whose initial values are matched with measured values. Sequence SEQ$(1000) is adapted to stored definitive base sequence, whose initial values are zero.

A sequence number NSEQ is initially set at 1, and a time number Nt is set at 2 (steps S1 and S2). Symbol Nt represent scan numbers in this embodiment.

The electrophoresis lane of A is assumed to be the reference lane, and a determination is made as to whether or not a signal A is a maximum signal (step $3). If the signal A is a maximum signal, it is assumed that SEQ$(NSEQ)=A and A(NSEQ)=Nt as base sequence (step 4). A determination is made as to whether or not there is a maximum signal of A ahead of this maximum, and if this maximum is the first one, 1 is added to the sequence number NSEQ as well as to the time number Nt (steps $5, $6, $7, $8 and $9), and the process returns to the step $3 to repeat the processing.

If the signal A is not a maximum signal, a determination is made as to whether or not there is a maximum signal in G, T or C in steps S10 to S12, and if there is no maximum signal, 1 is added to the time number Nt (steps) $8 and $9), and the same operation is repeated again. If a maximum signal is found in G, T or C, the bases are sequenced (steps S13, S14 and S15) and 1 is added to the sequence number NSEQ as well as to the time number Nt (steps S16, $8 and $9), and the process returns to the step $3 to repeat the processing.

Referring again to FIG. 3, the 11-th peak A appears at Nt=2020-th scanning and the 20-th peak A appears at Nt=2200-th scanning, and peaks of other electrophoresis lanes are also detected to evaluate maximum value data as shown in FIG. 5. The base sequence SEQ$(1000) is defined as AGTTC ... ... as shown in FIG. 5.

Figure 4:
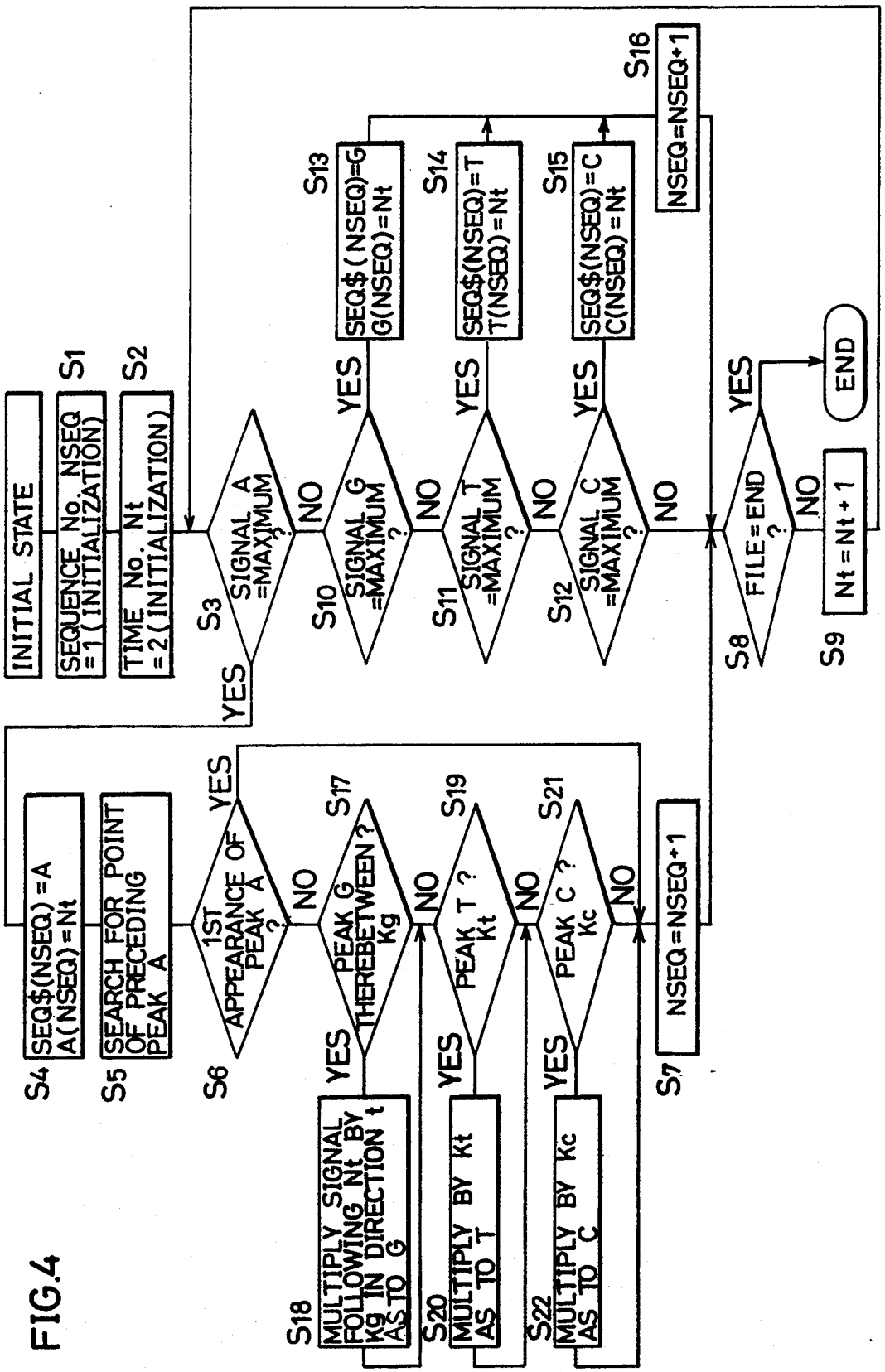
FIG. 4 is a flow chart showing procedure for calculating calibration coefficients.

Steps S17 to $22 shown in FIG. 4 are adapted to evaluate calibration coefficients. In the example shown in FIG. 3, the process advances to the step S17 upon appearance of the 20-th peak A to calculate scan numbers of enclosed peaks in FIG. 5, i.e., scan numbers of the 19-th peak C, the 18-th peak G and the 17-th peak T in proportional distribution as values attained on the assumption that the peaks appear at regular intervals (this corresponds to vertical lines in FIG. 3) and to take ratios thereof to measured scan numbers, thereby calculating calibration coefficients of the respective electrophoresis lanes of G, T and C.

In relation to the signals shown in FIG. 3, the peak time (scan number) of the actual signal is 2170 as to the electrophoresis lane G, and the peak time calculated in proportional distribution on the assumption that the peaks appear at regular intervals is 2160, whereby the calibration coefficient Kg for G is as follows:

$$Kg = 2160/2170 = 0.99539$$

Also as to the electrophoresis lane T, the calibration coefficient Kt is similarly calculated as follows:

$$Kt = 2140/2135 = 1.0023419$$

As to the lane C, the calibration coefficient Kc is equal to 1.

The respective calibration coefficients evaluated in the aforementioned manner are multiplied by the times of the respective sequence of RG, RT and RC following 2200, to rewrite date of RG, RT and RC and introduce the same to RG1, RT1 and RC1.

This procedure is repeated every appearance of the peak A.

Figure 6:
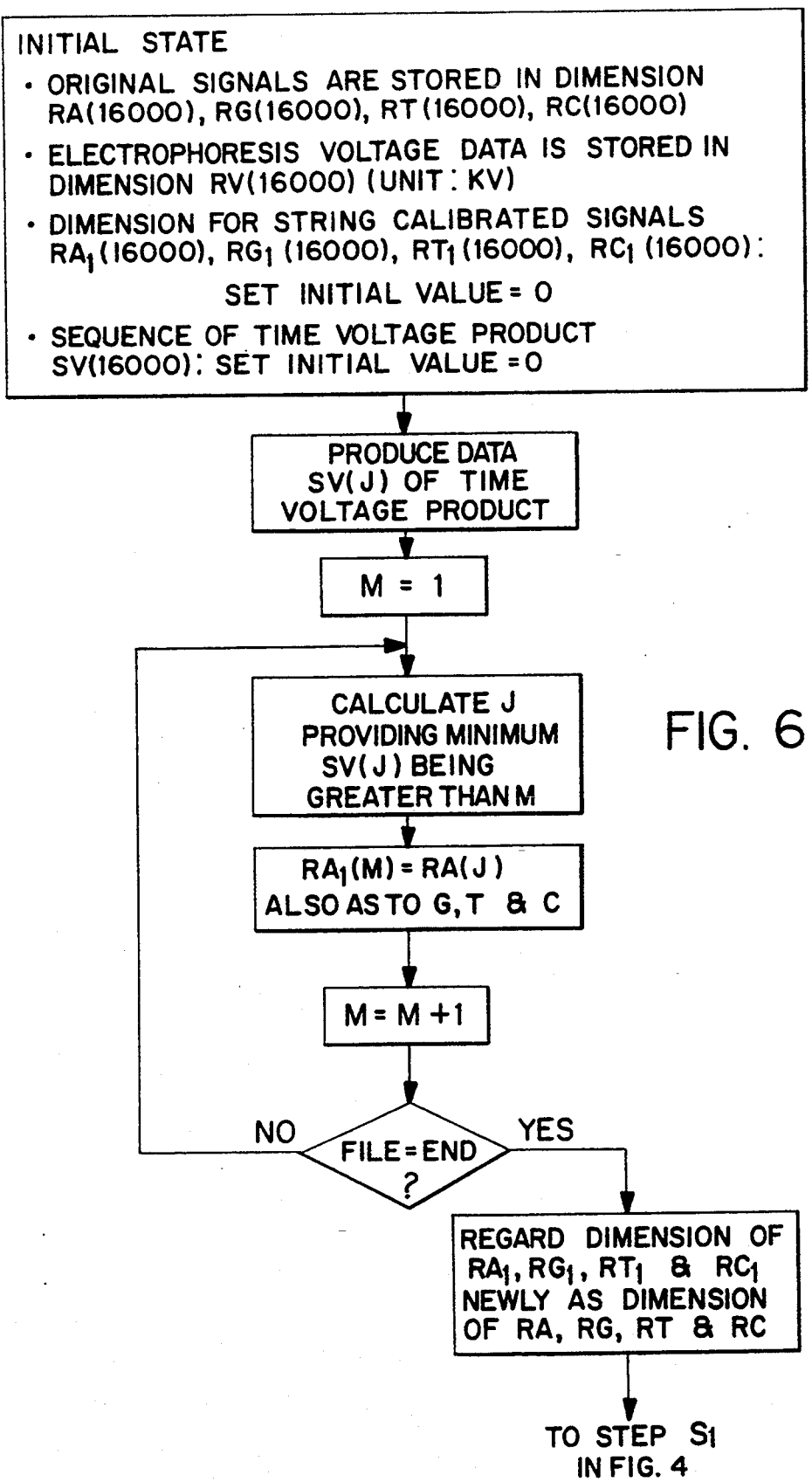
FIG. 6 is a flow chart showing the procedure of pretreatment for discontinuous electrophoresis conditions.

The flow chart shown in FIG. 4 is on the premise that the electrophoresis conditions are constant with constant voltage, constant current and constant power, for example, upon starting of electrophoresis at least from appearance of signals, while correction is required when the electrophoresis conditions are changes during electrophoresis, for example. FIG. 6 shows an exemplary data pretreatment method in relation to discontinuous change of electrophoresis conditions. In the example shown in FIG. 6, a data train is finally converted to electrophoresis data under a constant voltage of 1 Kv.

First, data of time voltage products are produced as to the respective times form measured electrophoresis voltage data RV(J) (unit: KV) as follows:

$$SV(J) = \sum_{k=0}^{J} RV(K) \quad \text{(unit: [Scan } KV\text{])}$$

where symbol SV(K) represents a monotone increasing function of J.

In order to evaluate respective date RAi(M), RGi(M), RT1(M) and RC1(M) (M=1 ...... 16000) of 1 KV constant voltage conversion values, the value of J providing the first SV(J) which is greater than M, for example, may be evaluated to apply values of original signals with respect to J. For example, RAI(M) =RA(J), RGi(M) =RG(J) ... ... .

After the pretreatment is performed according to the flow chart shown in FIG. 6, the process advances to the step S1 shown in FIG. 4.

Figure 7:
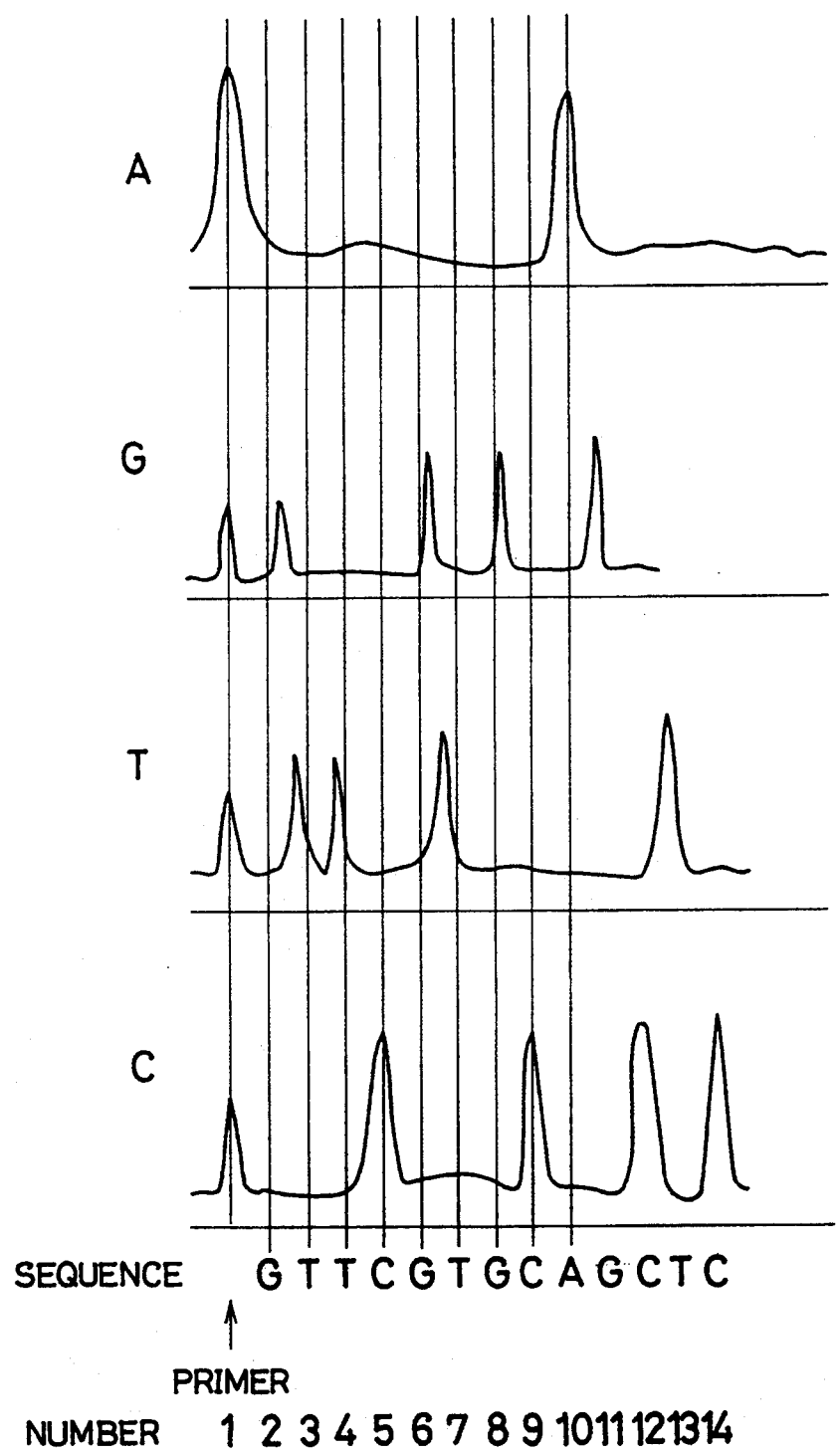
FIG. 7 illustrates exemplary detection signals in relation to fluorescent primers.
Figure 8:
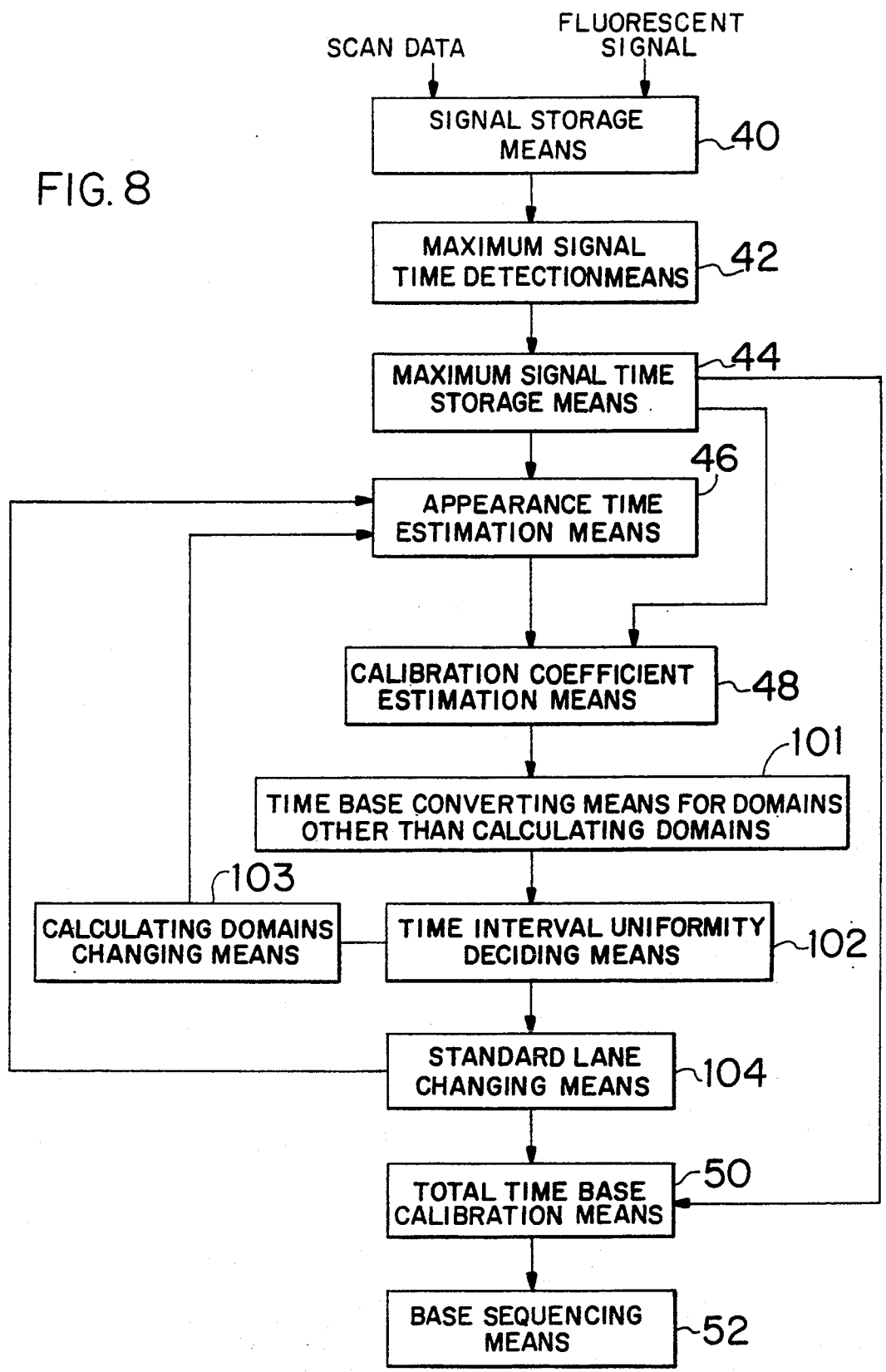
FIG. 8 is a block diagram showing functions of a signal processing microcomputer in an embodiment of the additional invention.

The first peak of the reference lane may be a fluorescent primer. In this case, peaks simultaneously appear at A, G, T and C of the first sequence numbers as shown in FIG. 7, for example. Also in this case, the flow chart shown in FIG. 4 requires no change but effectuates the same function.

In the flow chart shown in FIG. 4, the calibration coefficients are calculated every time a peak appears in the electrophoresis lane A, which is the reference lane, to repeat calibration of the time bases of the remaining three lanes. Alternatively, calibration coefficients once calculated in portions having relatively short base lengths, for example, may also be employed for portions having long base lengths.

The embodiment of the base sequencing apparatus is identical to that described with reference to FIG. 2.

Figure 10:
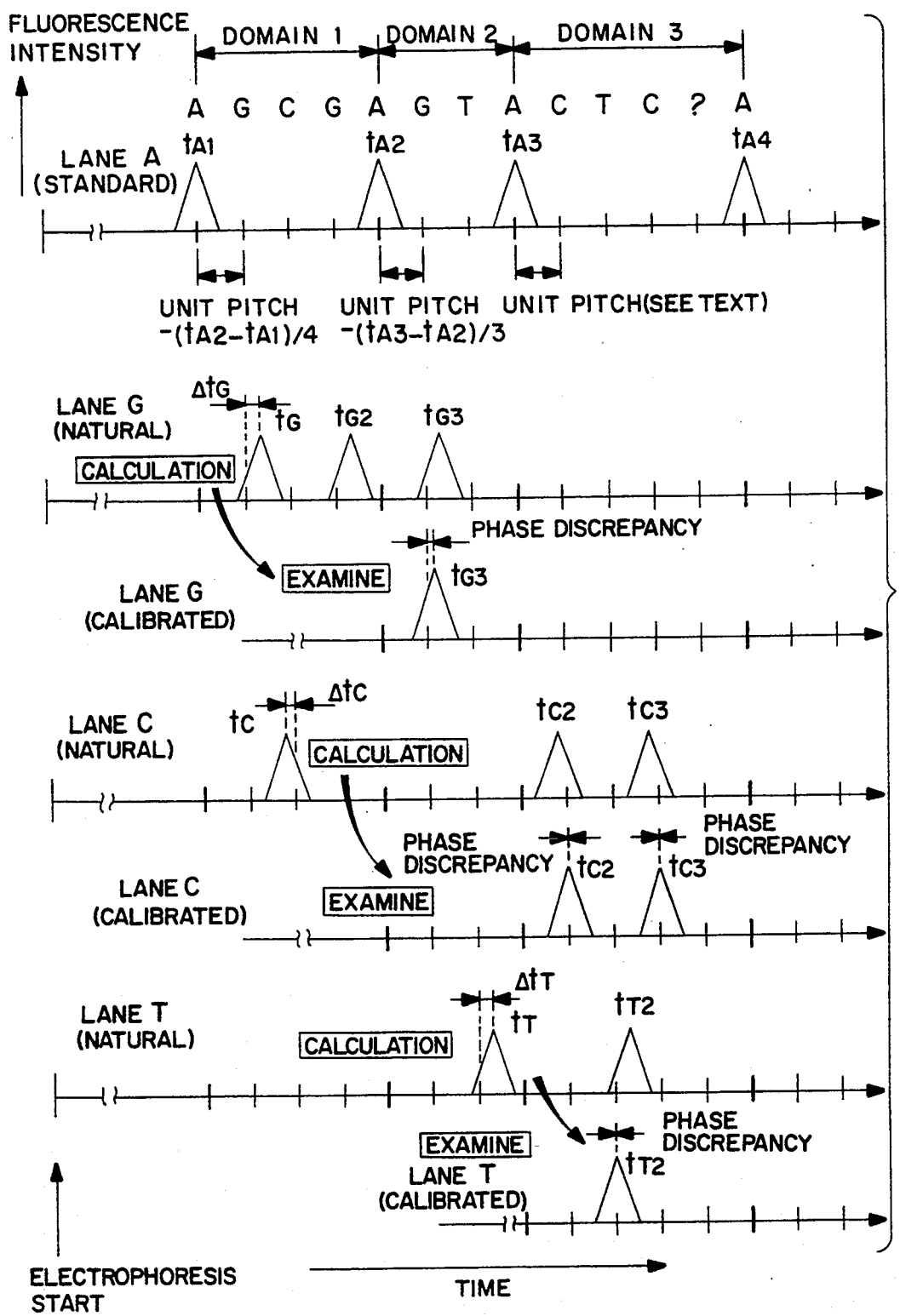
FIG. 10 illustrates signals of respective electrophoresis lanes measured in the embodiment.
Figure 11:
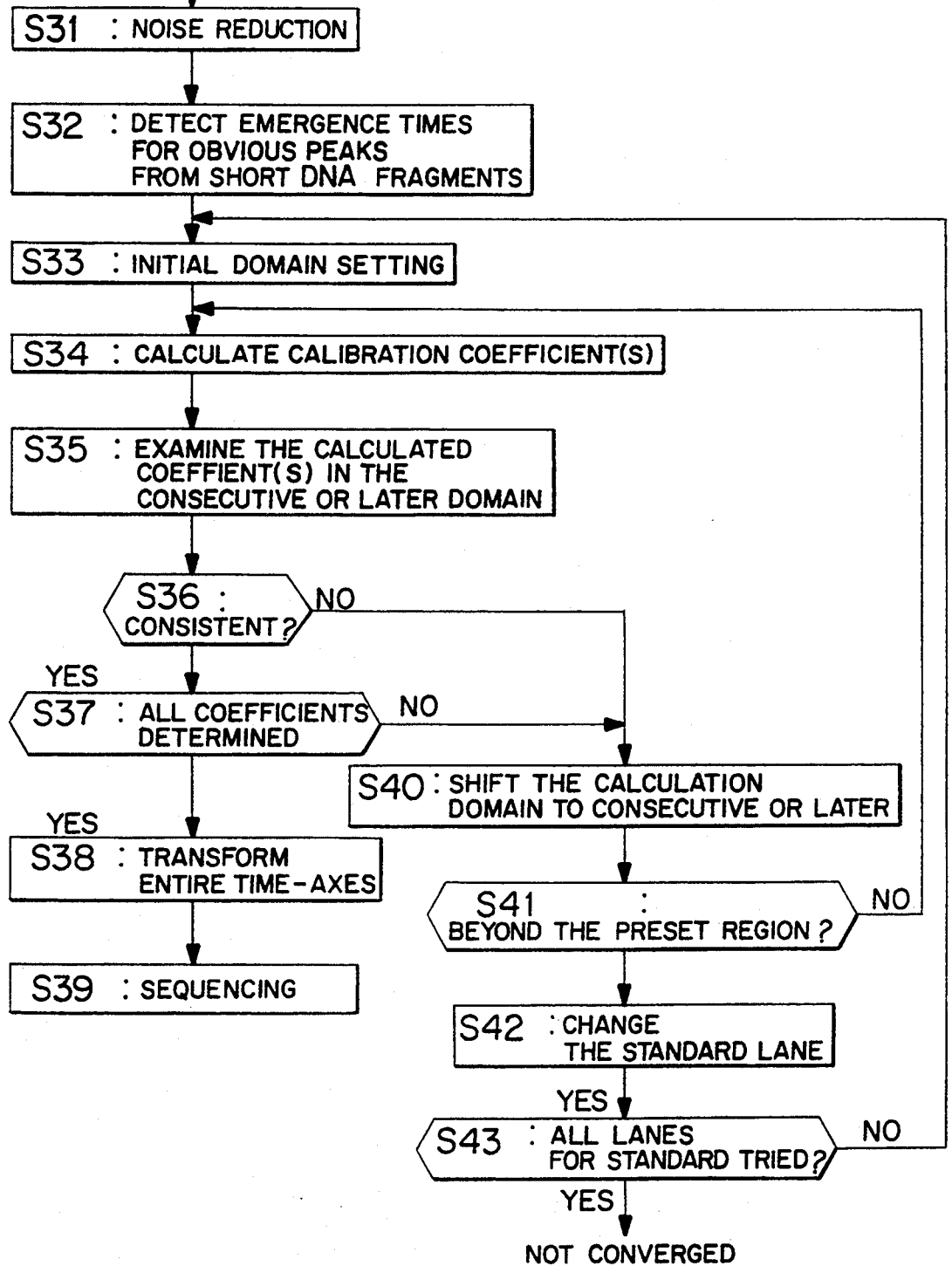
FIG. 11 is a flow chart showing the operation of the embodiment.

The operation of the embodiment shown in FIGS. 10 and 11 is now described.

FIG. 10 shows exemplary signals obtained in the base sequencing apparatus. Symbols A, G, T and C correspond to respective electrophoresis lanes, while times shown on the axis abscissas are in one-to-one correspondence to numbers of scanning operations made by optical systems perpendicularly to the electrophoresis direction.

FIG. 10 shows portions having relatively shore base lengths, and no inversion of signal appearance order (i.e. no sequence misreading is caused even if "smiling" takes place, since differences between electrophoresis speeds per base length are large). Referring to FIG. 10 in more detail, three peaks of G, C and G are present in domain 1. When lines are drawn on the assumption that three peaks appear between two peaks of A at regular intervals, it is understood that the peaks of G are delayed from the lines while the peak of C appears slightly ahead of the lines. When lines are similarly drawn in a domain 2, it is understood that a peak of T is delayed as compared with peaks of A.

Procedure form calibration of time bases to base sequencing is now described with standard to a flow chart shown in FIG. 11.

CALCULATION OF CALIBRATION COEFFICIENTS

A "smiling" calibration coefficient (i.e. mobility ratio with respect to a standard lane) is calculated for the short DNA fragments where peaks are clear and no emergence order exchange occurs (steps S31, S32, S33, S34). The standard lane can be chosen arbitrarily in principle, then if the program cannot determine the calibration coefficients, the standard lane will be exchanged (see Step S42).

Figure 9:
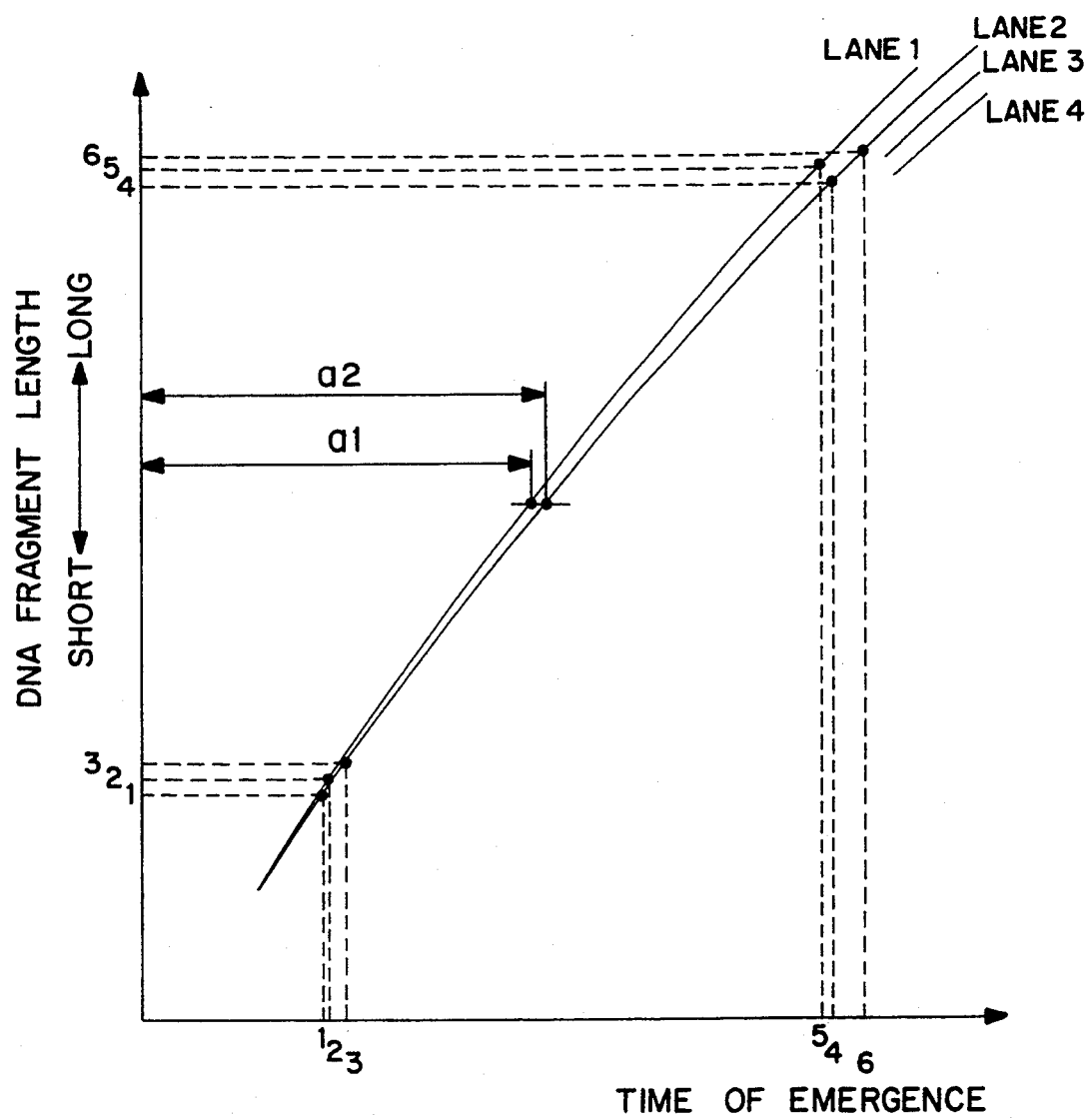
FIG. 9 illustrates relations between peak appearance times and DNA fragment base lengths.

In practice, sometimes G or C lane exhibits compressions, however, the algorithm will reject such region automatically. In the following explanation, assume lane A is determined as the standard. In FIG. 10, the dots in time-axes indicate the expected emergence time calculated under an assumption that the pitch of peak emergences is constant (=unit pitch) within a restricted period between two consecutive peaks in lane A (A—A domain). For example, in domain 1, unit pitch=((ta2-ta1)/4, where the devisor 4 corresponds to the number of peaks between the lane A peaks. This assumption means, within the A—A domain (order of 10-20 bases), each plot in FIG. 9 approximates to straight. The discrepancies between the expected and observed peak emergence times are indicated as Δtg, Δtc, and Δtt. In the first cycle, the domain for calculation is supposed to set to domain 1, then the calibration coefficient for lane G and C can be calculated at Δtg/tg and Δtc/tc, respectively. The coefficient for T lane will be calculated in the second cycle where the domain for calculation shifts to domain 2.

EXAMINATION OF COEFFICIENTS (STEPS S35, S36 AND S40)

The calculated coefficients are examined in the consecutive or later signal domain by checking the variance of pitches between the peak emergency times after applying the time axis transformation according to the calculated coefficients. The detail procedure is:
 (i) the time-axis of examined lanes (e.g. G and C lanes for the first cycle) are divided by the calculated coefficients.
 (ii) in order to calculate the peak number in an A—A period containing the consecutive peaks in the examined lane, the A—A period length is divided by the unit pitch in Step S34 and then the quotient is rounded to an integer, assuming unit pitch varies very slightly throughout.

lane G:
 peak number in domain 2 = $(ta3 - ta2)/\{(ta2 - ta1)/4\}$ integer lane C:
 peak number in domain 3 = $(ta4 - ta3)/\{(ta3 - ta2)/3\}$ integer (iii) in order to estimate the unit pitch around the examined peak ($tg3'$ or $tc2'$), the A—A period length is divided by the peak number form (ii).
 [unit pitch in dom. 2 =(ta3-ta2)/peak number in dom. 2 ]

This is a description of the algorithm generally. This will equal to (ta4-ta3)/4 in the example of FIG. 10.
 [unit pitch in dom. 3 =( ta4-ta3 )/peak number in dom. 3 ]
 (iv) pitch between the examined peak and the previous A peak is divided by the unit pitch of (iii). The decimal fraction after integer subtraction of the quotient represents phase discrepancy of peak emergency, which can judge the consistency.

lane G:
 phase discrepancy = $[(tg3' - ta2)/\text{unit pitch in domain 2}]$
 (decimal fraction)

lane C:
 phase discrepancy = $[(tc2' - ta3)/\text{unit pitch in domain 3}]$
 (decimal fraction)

(v) if the phase discrepancy of (iv) is near 0 or 1 (in this experiment, the error allowance was set to one unit of time-axis resolution), the calculated "smiling" coefficient is regarded as correct. If not, regarded as wrong, the A—A domain for calculation is changed to the consecutive one and the program goes back to step 2 for re-calculation (step S36, S40).

STANDARD LANE EXCHANGE (STEP S42)

If the repeated calculation/examination procedures leads the calculating domain out of the preset short nucleotide region (in the experiments, the region is set to: 1500-2012 scan, i.e., 2 hours and 5 minutes to 2 hours and 47 minutes sample electrophoresis, where emergency order exchange never occurs), the standard lane will be changed to retry (in the experiments, programmed as A→T→G→C).

TIME-AXIS TRANSFORMATION (STEP S38)

The entire time-axes are transformed according to the calibration coefficients calculated and examined by the above algorithm, then sequence are obtained from the transformed data.

Thus, the calibration coefficients are so examined that correct ones are employed for improving accuracy in base sequencing.

The data processing unit of the base sequencing apparatus according to the present invention can be programmed with conventional computer software to carry out the above described functions in various manners. One skilled in the art of programming equipment of this nature can design the requisite program without undo experimentation, or without special skill or knowledge based on the information contained in this disclosure.

Although the present invention has been described and illustrated in detail, it is clearly understood that the same is by way of illustration and example only and is not to be taken by way of limitation, the spirit and scope of the present invention being limited only by the terms of the append claims.

I claim:

1. A base sequencing apparatus for dividing labelled nucleic acid fragment samples into four electrophoresis lanes in response to types of end bases and simultaneously gel-electrophoresing said samples while scanning signals outputted form said nucleic acid fragment samples in a direction perpendicular to the electrophoresis direction for acquiring said signals in on-line real time, thereby sequencing bases in a data processing unit, wherein said data processing unit evaluates calibration coefficients of time bases of respective said electrophoresis lanes from differences between positions of signals being already outputted in a range causing no sequence inversion and positions of substantially regular intervals for originally outputting signals, for calibrating time bases as to respective subsequent electrophoresis lanes with said calibration coefficients.

2. A base sequencing apparatus for dividing labelled nucleic acid fragment samples into four electrophoresis lanes in response to types of end bases and simultaneously gel-electrophoresing said samples while scanning signals outputted from said nucleic acid fragment samples in a direction perpendicular to the electrophoresis direction for acquiring said signals in on-line real time, thereby sequencing bases in a data processing unit, wherein said data processing unit comprises:

signal storage means for storing signals form respective said electrophoresis lanes with respect to time;

maximum signal detection means for detecting times providing maximum values of said signals as to respective said electrophoresis lanes;

maximum signal time storage means for storing said maximum signal times;

appearance time estimation means selecting one of said four electrophoresis lanes as a reference lane and assuming that there is no difference of mobility between said electrophoresis lanes for calculating appearance times of maximum signals of the remaining three electrophoresis lanes appearing between two maximum signals of said reference lane on the time base of the reference lane;

calibration coefficient calculation means for calculating calibration coefficients from ratios of said maximum signal times of said three electrophoresis lanes calculated in said appearance time estimation means to actual maximum signal times;

time base calibration means for calibrating said time bases of said three electrophoresis lanes with said calibration coefficients; and base sequencing means for sequencing bases from said maximum signal times of said reference lane and said three electrophoresis lanes based on calibrated said time bases.

3. A base sequencing apparatus in accordance with claim 2, wherein said appearance time estimation means performs calculation on the assumption that said maximum signals of said three electrophoresis lanes appear between two maximum signals of said reference lane at regular time intervals.

4. A base sequencing apparatus in accordance with claim 2, wherein said calibration coefficient calculation means calculates said calibration coefficients every time a maximum signal appears on said reference lane between said signal and a preceding maximum signal of said reference lane, and said time base calibration means calibrates said time bases of said three electrophoresis lanes being effective until a next maximum signal appears on said reference lane.

5. A base sequencing apparatus in accordance with claim 2, wherein said calibration coefficient calculation means once calculates calibration coefficients in portions having short base lengths, and said time base calibration means calibrates said times bases with said calibration coefficients with respect to portions having long base lengths.

6. A base sequencing apparatus in accordance with claim 1, further comprising means for converting time bases in such a case that electrophoresis conditions are changed to time bases in such manner that electrophoresis conditions are constant.

7. A base sequencing apparatus in accordance with claim 2, further comprising means for converting time bases in such a case that electrophoresis conditions are changed to time bases in such a case that electrophoresis conditions are constant.

8. A base sequencing apparatus for dividing labelled nucleic acid fragment samples, comprising:

four electrophoresis lanes for accepting different types of end bases;

excitation and detection system for scanning signals outputted from the labelled nucleic acid fragment samples for acquiring said signals; and a calibration unit for calibrating said signals in real time to eliminate the effects of smiling to more accurately read a base sequence than a base sequencing apparatus not provided with such a signal calibration unit.

9. A base sequencing apparatus according to claim 8, wherein said signal calibration unit evaluates the calibration coefficients of time values of the bases in the respective electrophoresis lanes to determine the rate coefficients of the electrophoresis lanes from differences between positions of detected signals already outputted in a range determined to cause no sequence inversion.

10. A base sequencing apparatus according to claim 9, wherein said signal calibration unit includes a data processing unit, said date processing unit, comprising:

signal storage means for storing signals from respective electrophoresis lanes with respect to time values;

maximum signal detection means for detecting time values providing maximum values of said signals as to respective electrophoresis lanes;

maximum signal storage means for storing maximum signal time values;

appearance time estimation means selecting one of said electrophoresis lanes as a reference lane and assuming that there is no difference of mobility between said electrophoresis lanes for calculating appearance time values of maximum signals of the remaining three electrophoresis lanes appearing between two maximum signals of said reference lane on the time basis of the reference lane;

calibration coefficient calculation means for calculating calibration coefficients from ratios of said maximum signal time values of said three electrophoresis lanes calculated in said appearance time estimation means to actual maximum signal time values;

time base calibration means for calibrating said time basis of said three electrophoresis lanes with said calibration coefficients; and base sequencing means for sequencing bases from said maximum signal time values of said reference lane and said three electrophoresis lanes based on calibrated said time values basis.

11. A base sequencing apparatus according to claim 8, wherein said signal calibration unit includes a data processing unit, said date processing unit, comprising:

signal storage means for storing signals from respective electrophoresis lanes with respect to time values;

maximum signal detection means for detecting time values providing maximum values of said signals as to respective electrophoresis lanes;

maximum signal storage means for storing maximum signal time values;

appearance time estimation means selecting one of said electrophoresis lanes as a reference lane and assuming that there is no difference of mobility between said electrophoresis lanes for calculating appearance time values of maximum signals of the remaining three electrophoresis lanes appearing between two maximum signals of said reference lane on the time basis of the reference lane;

calibration coefficient calculation means for calculating calibration coefficients from ratios of said maximum signal time values of said three electrophoresis lanes calculated in said appearance time estimation means to actual maximum signal time values;

time base calibration means for calibrating said time basis of said three electrophoresis lanes with said calibration coefficients; and base sequencing means for sequencing bases from said maximum signal time values of said reference lane and said three electrophoresis lanes based on calibrated said time values basis.

12. A base sequencing apparatus according to claim 8, wherein said excitation and detection system scans said signals outputted from the labelled nucleic acid fragment samples in a direction perpendicular to an electrophoresis direction.

13. A base sequencing apparatus according to claim 12, wherein said excitation and detection system comprises a laser with means for directing a laser beam onto a electrophoresis gel selectively at four bands in a direction perpendicular to said electrophoresis direction, and a photomultiplier for detecting said signals outputted from the nucleic acid fragment.

14. A base sequencing apparatus according to claim 8, wherein said calibration unit comprises a computer, and including an amplifier and A/D converter connected between said photomultiplier and said computer.

15. A base sequencing apparatus according to claim 13, wherein said laser beam directing means comprises an obliquely positioned mirror relative to said laser and a condenser positioned therebetween mounted on a scanning stage which is reciprocated in a direction perpendicular to said electrophoresis direction, and an objective lens, interference filter and condenser lens is positioned in a sequence between said electrophoresis gel and said photomultiplier.

16. A base sequencing apparatus for dividing labelled nucleic acid fragment samples, comprising:

four electrophoresis lanes for dividing the labelled nucleic acid fragment samples in response to types of end bases and for simultaneously gel-electrophoresing said samples;

scanning means for scanning signals outputted form said nucleic acid fragment samples in a direction perpendicular to the electrophoresis direction for acquiring said signals in on-line real time;

a data processing unit for sequencing bases in on-line real time, said data processing unit comprising:

signal storage means for storing signals from respective electrophoresis lanes with respect to time;

maximum signal time detection means for detecting time values and providing maximum values of said signal of respective electrophoresis lanes;

appearance time estimation means selecting one of said electrophoresis lanes as a standard lane and assuming that there is no difference of mobility between said electrophoresis lanes for calculating appearance times of maximum signals of the remaining electrophoresis lanes appearing between two maximum signals of said standard lane with the time base of said standard lane;

calibration coefficient calculating means for calculating calibration coefficients from ratios of said maximum signal times of said three electrophoresis lanes calculated in said appearance time estimation means to actual maximum signal times;

means for converting time bases of signals in time domains other than those used for calculating said calibration coefficients through calculated calibration coefficients;

means for deciding validity of said calibration coefficients depending on whether or not converted said signals appear at uniform time intervals;

total time base calculation means for calibrating total time bases of said electrophoresis lanes with calibration coefficients being decided as valid; and base sequencing means for sequencing bases from said maximum signal times of said four electrophoresis lanes based on calibrated time bases.

17. A base sequencing apparatus according to claim 16, wherein said means for deciding validity of said calibration coefficients makes a decision of inadequacy when diffusion or standard deviation of difference between estimated appearance times of calculated peaks and actual appearance times of converted signals exceeds a constant value.

18. A base sequencing apparatus according to claim 16, further comprising means for changing said standard lane when all said calibration coefficients of said three lanes are not decided to be valid as to set said standard lane.

* * * * *